United States Patent [19]

Beg

[11] 4,089,970

[45] May 16, 1978

[54] METHOD OF INHIBITING PLATELET AGGREGATION

[75] Inventor: Mirza M. A. Beg, Melrose Park, Pa.

[73] Assignee: SmithKline Corporation, Philadelphia, Pa.

[21] Appl. No.: 831,322

[22] Filed: Sep. 7, 1977

[51] Int. Cl.² .................. A61K 31/38; A61K 31/495
[52] U.S. Cl. .................................. 424/275; 424/250
[58] Field of Search .......................... 424/275, 250

[56] References Cited

U.S. PATENT DOCUMENTS

| 3,758,506 | 9/1973 | Godfroid et al. | 424/275 |
| 3,958,004 | 5/1976 | Cragoe et al. | 424/275 |
| 3,969,508 | 7/1976 | Di Tulbo et al. | 424/275 |
| 3,969,529 | 7/1976 | Godfroid et al. | 424/275 |
| 3,989,838 | 11/1976 | Maass | 424/275 |
| 4,005,095 | 1/1977 | Robba et al. | 424/275 |
| 4,017,632 | 4/1977 | Nachnvas et al. | 424/275 |

OTHER PUBLICATIONS

J. Atheroscler, Res., 1969, 10: pp. 33-39.

*Primary Examiner*—Donald B. Moyer
*Attorney, Agent, or Firm*—Richard D. Foggio; William H. Edgerton

[57] ABSTRACT

Method of inhibiting platelet aggregation by administering 4-(2-thenoyl)-2,3-dichlorophenoxyacetic acid or its salts.

5 Claims, No Drawings

METHOD OF INHIBITING PLATELET AGGREGATION

This invention relates to a novel method of inhibiting platelet aggregation which comprises administering nontoxic effective quantities of an active ingredient which inhibits platelet aggregation to a subject in need thereof. More specifically, the active ingredient used in the methods of this invention is 4-(2-thenoyl)-2,3-dichlorophenoxyacetic acid (also known as ticrynafen) having the following formula:

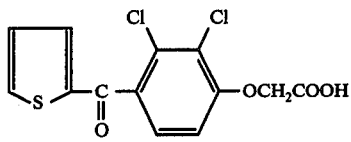

FORMULA I or an alkali metal salt of said acid, for example the sodium or potassium salt, or a pharmaceutically acceptable, nontoxic addition salt of said acid formed with a base, for example the piperazine or (trihydroxymethyl) methylamine salt.

The acid of formula I and its preparation is described in U.S. Pat. No. 3,758,506. Generally, 2,3-dichloroanisole is condensed with thiophene-2-carboxylic acid chloride in the presence of aluminum chloride, the resulting ketone is demethylated and the hydroxy ketone is reacted with an ester of chloroacetic acid to give the product after hydrolysis of the ester. The compound is disclosed as having diuretic activity.

The acid of formula I is also known to lower the concentration of plasma triglycerides (U.S. Pat. No. 3,969,508) and produce uricosuria (U.S. Pat. No. 3,958,004).

Platelet aggregation may be a contributing factor in coronary heart disease and other thromboembolic complications associated with hypertension. Therefore, inhibition of platelet aggregation would be useful in the treatment of hypertension. The effect of 4-(2-thenoyl)-2,3-dichlorophenoxyacetic acid on platelet aggregation has been demonstrated both in vitro and in vivo. The aggregation studies were performed in vitro under conditions similar to those described in Lin et al. Life Sciences 18:563–568, 1976. Human platelets obtained from two different subjects were used and ticrynafen (as the tris salt) was tested against adenosine diphosphate, (ADP), collagen and epinephrine induced platelet aggregation. Each incubation contained 0.4 ml. of human platelet rich plasma, 0.05 ml. of the drug solution or distilled water (control). The mixture was incubated for 3 minutes in a Bio/data aggregometer at 37° C. with stirring and 0.05 ml. of platelet aggregation inducer was added. The working solution of the tris salt of ticrynafen contained 8 mg. of the drug per ml. (24 mM).

The results of testing the tris salt of ticrynafen as described above are summarized in Table I.

TABLE I

| Inducer | Tris Ticrynafen (ug/ml) | Effect |
|---|---|---|
| Collagen (2 μ/ml) | 160 | Slight delay of aggregation |
| | 320 | Delay of aggregation and extent of aggregation decreased. |
| Epinephrine | 160 | No effect. |

TABLE I-continued

| Inducer | Tris Ticrynafen (ug/ml) | Effect |
|---|---|---|
| (2.5 μg/ml) | 320 | Delay of second wave. |
| | 480 | Additional delay of second wave. |
| ADP (2 μm/ml) | 160 | Second wave slightly delayed. |
| | 320 | Second wave more delayed. |
| | 480 | Second wave eliminated. |

It is clear from these results that ticrynafen has an inhibitory effect on aggregation of human platelets.

In an in vivo experiment, the aggregation of platelets, induced by 1 μg/ml of collagen, from a human patient taking 250 mg. of ticrynafen daily for 7 months was compared with that of a normal control. Platelet count in platelet rich plasma (PRP) was adjusted to 300,000 platelets/ml., 0.45 ml. of PRP was incubated at 37° C. for 3 minutes and then 0.05 ml. of inducer was added. Under these conditions, platelet aggregation was almost completely inhibited in the ticrynafen treated patient as compared to the control. ADP induced platelet aggregation was also inhibited in the ticrynafen treated patient at a concentration of 4 μM ADP. Epinephrine induced platelet aggregation at a concentration of 5 μg/ml of epinephrine did not appear to be inhibited. It is believed that collagen induced aggregation of platelets is the most significant for a hypertensive patient.

The method in accordance with this invention comprises administering internally to an animal subject in need of inhibition of platelet aggregation the compound 4-(2-thenoyl)-2,3-dichlorophenoxyacetic acid or a salt thereof, usually combined with a pharmaceutical carrier, in a nontoxic quantity selected from about 100 mg. to about 500 mg. of the parent chemical of formula I. The route of administration may be orally or parenterally, the oral route being preferred. Conveniently equal doses will be administered two to four times daily with the daily dosage regimen being from about 200 mg. to about 2000 mg. When the method described above is carried out, inhibition of platelet aggregation is produced.

The dosage units employed in the above described method are in conventional forms and are prepared by incorporating the active ingredient with a nontoxic pharmaceutical carrier according to accepted procedures.

The pharmaceutical carrier may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to the desired end product. The following examples illustrate the preparation of such compositions used in the method of this invention.

| Ingredients | Mg/Tablet |
| --- | --- |
| 4-(2-thenoyl)2,3-dichloro-phenoxyacetic acid | 250 |
| Corn starch | 30 |
| Polyvinyl pyrrolidone | 12 |
| Corn starch | 16 |
| Magnesium stearate | 3 |

The first two ingredients are thoroughly mixed and granulated with a 20% w/v solution of polyvinyl pyrrolidone in water. The wetted mass is passed through a No. 4 mesh screen directly only drying trays. The granules are dried at 50° C. and mixed with the remaining corn starch and magnesium stearate, and compressed into tablets. The tablets are administered to a subject in need of inhibition of platelet aggregation 3 times daily.

| Ingredients | Mg/Capsule |
| --- | --- |
| 4-(2-thenoyl)-2,3-dichloro-phenoxyacetic acid | 500 |
| Magnesium stearate | 2 |
| Lactose | 50 |

The above ingredients are screened through a No. 40 mesh screen, mixed and filled into No. 0 hard gelatin capsules. The capsules are administered to a subject in need of inhibition of platelet aggregation twice daily.

What is claimed is:

1. A method of inhibiting platelet aggregation which comprises administering internally to an animal subject in need of said inhibition a nontoxic amount sufficient to produce said inhibition of the compound 4-(2-thenoyl)-2,3-dichlorophenoxyacetic acid, an alkali metal salt of said acid or a pharmaceutically acceptable addition salt of said acid formed with a base.

2. The method of claim 1 in which a daily dosage of from about 200 mg. to about 2000 mg. of active ingredient is administered.

3. The method of claim 1 in which the active ingredient is administered with a pharmaceutical carrier in dosage unit form.

4. The method of claim 3 in which dosage units containing from about 100 mg. to about 500 mg. of the active ingredient are administered 2 to 4 times daily.

5. The method of claim 4 in which the administration is orally.

* * * * *